United States Patent [19]
French et al.

[11] Patent Number: 6,095,997
[45] Date of Patent: Aug. 1, 2000

[54] INTRALUMINAL SHUNT AND METHODS OF USE

[75] Inventors: Fritz French, Menlo Park; Hugh L. Narciso, Jr., Mountain View, both of Calif.; Troy Chapman, Avilla, Ind.; Mike Hogendijk, Palo Alto, Calif.

[73] Assignee: Corvascular, Inc., Palo Alto, Calif.

[21] Appl. No.: 09/034,849

[22] Filed: Mar. 4, 1998

[51] Int. Cl.[7] .......................... A61M 5/00; A61M 11/00; A61M 29/00; A61M 5/178; A61F 2/04
[52] U.S. Cl. ................ 604/9; 604/93; 604/104; 604/169; 604/284; 604/507; 623/12
[58] Field of Search .................. 604/8–9, 43, 93, 604/104, 175, 264, 502, 507, 523, 169, 284; 623/1, 12

[56] References Cited

U.S. PATENT DOCUMENTS

| | | | |
|---|---|---|---|
| H85 | 7/1986 | Shortsleeve | 604/284 |
| 4,712,551 | 12/1987 | Rayhanabad . | |
| 4,734,094 | 3/1988 | Jacob et al. | 604/284 |
| 4,822,341 | 4/1989 | Colone . | |
| 4,983,162 | 1/1991 | Metais et al. | 604/43 |
| 5,224,938 | 7/1993 | Fenton, Jr. | 604/9 |
| 5,549,651 | 8/1996 | Lynn | 604/169 |
| 5,607,393 | 3/1997 | Ensminger et al. . | |
| 5,695,504 | 12/1997 | Gifford, III et al. . | |
| 5,807,356 | 9/1998 | Finch, Jr. et al. | 604/284 |
| 5,824,071 | 10/1998 | Nelson et al. | 604/8 |

FOREIGN PATENT DOCUMENTS

| | | |
|---|---|---|
| 0 674 914 A1 | 10/1995 | European Pat. Off. . |
| 0 791 332 | 8/1997 | European Pat. Off. . |
| WO 96/40359 | 12/1996 | WIPO . |
| WO 97/12643 | 4/1997 | WIPO . |
| WO 97/20584 | 6/1997 | WIPO . |

OTHER PUBLICATIONS

Borst, C. et al., Coronary artery Bypass Grafting Without Cardiopulmonary Bypass and Without Interruption of Native Coronary Flow Using a Novel Anastomosis Site Restraining Device (Octopus), JAAC, 1996; 27;1356–64.

Boonstra, P. et al., Improved Method for Direct Coronary Grafting Without CPB via Anterolateral Small Thoracotomy, Ann. Thorac. Surg., 1997; 63:567–9.

Carrel, T. et al., Use of an Intraluminal Shunt to Repair a Coronary Bypass Graft Injury During Resternotomy, J. Thorac. Cardiovasc. Surg., 1995; 109:178–9.

Levinson, M. et al., Coronary Grafting Using a Temporary Intraluminal Shunt Instead of Heart–Lung Bypass, Ann. Thorac. Surg., 1995; 60:1801–3.

Rivetti, L. et al., Initial Experience Using an Intraluminal Shunt During Revascularization of the Beating Heart, Ann. Thorac. Surg. 1997; 63:1742–7.

(List continued on next page.)

*Primary Examiner*—John G. Weiss
*Assistant Examiner*—Patricia Bianco
*Attorney, Agent, or Firm*—Morrison & Foerster LLP

[57] ABSTRACT

The present invention is directed to intraluminal shunt devices and methods of their use for delivering a drug or other fluid to a target vessel of a patient while also maintaining perfusion of blood through the vessel to reduce ischemia downstream of the vessel. The intraluminal shunt devices may generally include a primary elongate tubular member that is sized and dimensioned to be inserted into the target vessel, such as the right coronary artery. The primary tubular member includes at least one inner lumen which permits blood perfusion through the vessel. At least one secondary tubular member is provided which is in fluid communication with the primary tubular member. The secondary tubular member may be configured for drug or fluid delivery through the primary tubular member and into the vessel in either an anterograde or retrograde direction. Methods of using shunt devices are also described which generally include making an incision in the target vessel, inserting the proximal and distal ends of the primary tubular member into the target vessel via the incision, and selectively delivering the drug or fluid in either an anterograde or retrograde direction through the primary tubular member and into the vessel.

28 Claims, 7 Drawing Sheets

OTHER PUBLICATIONS

Van Voorst, S. et al., Intraluminal Shunt for the Thoracic Aorta: Blood Flow and Function in Chronic Studies, Ann. Thorac. Surg., 1997; 63:419–22.

NeuroCare Group™ Heyer–Schulte®, Rivetti–Levinson™ Intraluminal Shunt, ©Copyright 1997 Heyer–Schulte NeuroCare.

Biovascular "Flo–Rester® Internal Vessel Occluder" p. 1 of 2, *Product Brochure*.

Ceres SV System "CTS™ Products" pp. 1 and 2 of 3, *Product Brochure*.

Medtronic "Breaking Tradition is Our Tradition" *Product Brochure*.

Medtronic "Distal Perfusion Kit" *Product Brochure*.

Medtronic "Intravascular Arteriotomy Cannulae" *Product Brochure*.

Medtronic "Introducing Medtronic InCardia™ Systems" *Product Brochure*.

Medtronic "The Medtronic InCardia™ CABG System" p. 1 of 2, *Product Brochure*.

INTRALUMINAL SHUNT AND METHODS OF USE

TECHNICAL FIELD

The present invention relates generally to surgical drug delivery devices and methods for delivering a drug or fluid into a vessel of a patient undergoing a surgical procedure, such as a coronary artery bypass graft procedure. More particularly, the present invention relates to intraluminal shunt devices for delivering a drug or fluid to the vessel of the patient, such as the right coronary artery, while also maintaining blood perfusion through the vessel.

BACKGROUND OF THE INVENTION

Minimally invasive surgical techniques have revolutionized cardiac surgery. Minimally invasive cardiac surgery enjoys the advantages of reduced morbidity, quicker recovery times, and improved cosmesis over conventional open-chest cardiac surgery. Recent advances in endoscopic instruments and percutaneous access to a patient's thoracic cavity have made minimally invasive surgery possible. Reduction in morbidity, lower cost, and reduced trauma has made minimally invasive surgery desirable.

One approach to minimally invasive cardiac surgery is coronary artery bypass grafting ("CABG") on a beating heart. At present, safe, reproducible, and precise anastomosis between a stenotic coronary artery and a bypass graft vessel presents numerous obstacles including myocardial ischemia (or arrhythmia induced by the transient period of coronary artery occlusion necessary for coronary arrest), significant bleeding into the operative field from septal bleeders despite adequate epicardial coronary artery occlusion, inability to graft the left circumflex system due to hemodynamic sequelae induced by lifting the heart, and continuous cardiac translational motion which may impair meticulous microsurgical placement of graft sutures.

For CABG on a beating heart to be universally accepted, the superior patency rates of the internal thoracic artery to the left anterior descending artery (LAD) can not be compromised. A major obstacle to safe and precise coronary anastomosis is the constant motion of the beating heart. Surgical approaches have been developed to stabilize the heart and facilitate anastomosis. Most new approaches employ some form of mechanical stabilization to stabilize the beating heart, such as the "fork-shaped" coronary artery stabilizer manufactured by Cardio Thoracic Systems, Inc. and described in Boonstra, P. W., Grandjean J. G., Mariani, M. A., *Improved Method for Direct Coronary Grafting Without CPB Via Anterolateral Small Thoracotomy*, Ann. Thorac. Surg. 1997;63:567–9. The coronary artery stabilizer in combination with an access platform in which it sits helps stabilize the left anterior descending artery on the beating heart and permits an arteriotomy with a conventional scalpel and scissors. In addition, many other different technologies that allow local coronary wall immobilization have been developed including various platform devices and the Utrecht "Octopus" device in which suction pods are placed adjacent the coronary artery. The suction immobilization simulates the arrested condition locally (see, e.g., Borst C., Jansen E. W. L., Tulleken C. A. F., et al., *Coronary Artery Bypass Grafting Without Cardiopulmonary Bypass and Without Interruption of Native Coronary Flow Using a Novel Anastomosis Site Restraining Device* ("*Octopus*"), J. Am. Coll. Cardiol. 1996;27:1356–64).

However, precise vascular anastomosis using mechanical stabilization techniques remains elusive due in large part to the inherent difficulties in maintaining uniform and steady pressure on opposite sides of the LAD. Moreover, the constant translational motion of the heart and bleeding from the opening in the coronary artery hinder precise suture placement in the often tiny coronary vessel. Although bleeding can be reduced by using proximal and distal coronary occluders, by excluding diagonal and septal branches near the arterial opening when possible, and by continuous saline irrigation or humidified carbon dioxide insufflation, the incessant motion of the beating heart remains the Achilles' heel of minimally invasive coronary artery bypass surgery.

In response to problems associated with mechanical stabilization techniques, a new technique has been developed to minimize the cardiac motion which employs a novel pharmaceutical approach to stabilizing the heart. This revolutionary pharmaceutical approach to cardiac stabilization is described in co-pending provisional patent application Ser. No. 60/055,127 for Compositions, Apparatus and Methods For Facilitating Surgical Procedures, filed Aug. 8, 1997 and invented by Francis G. Duhaylongsod. M.D, the entire contents of which are expressly incorporated by reference herein. As described therein, pharmaceutical compositions and methods are provided which are useful for medical and surgical procedures which require precise control of cardiac contraction, such as coronary artery bypass procedures. In a preferred embodiment of that invention, a pharmaceutical composition is provided that is capable of inducing reversible ventricular asystole in a patient, while maintaining the ability of the heart to be electrically paced. "Reversible ventricular asystole" refers to a state wherein autonomous electrical conduction and escape rhythms in the ventricle are suppressed. A state of the heart may be induced wherein the heart is temporarily slowed to at least about 25 beats per minute or less, and often about 12 beats per minute or less. The induced ventricular asystole is reversible and after reversal, the heart functions are restored, and the heart is capable of continuing autonomous function.

The pharmaceutical composition may include, for example, an atrioventricular ("AV") node blocker and a beta blocker. As used herein, the term "AV node blocker" refers to a compound capable of reversibly suppressing autonomous electrical conduction at the AV node, while still allowing the heart to be electrically paced to maintain cardiac output. Preferably, the AV node blocker, or the composition comprising the AV node blocker, reduces or blocks ventricular escape beats and cardiac impulse transmission at the AV node of the heart, while the effect on depolarization of the pacemaker cells of the heart is minimal or nonexistent. The beta blocker is provided in one embodiment in an amount sufficient to substantially reduce the amount of AV node blocker required to induce ventricular asystole. For example, the AV node blocker may be present in the composition in an amount which is 50% or less by weight, or optionally about 1 to 20% by weight of the amount of AV node blocker alone required to induce ventricular asystole.

The pharmaceutical composition, such as an AV node blocker, capable of causing ventricular asystole in a preferred embodiment is a cholingeric agent such as carbachol, although other cholingeric agents may be used as well. In the preferred embodiment, the beta blocker is propranolol, although other suitable beta blockers may be used as well. The administration of the beta blocker is preferably prior to, or contemporaneously with, the administration of the cholinergic agent, and results in a synergistic effect between the beta blocker and the cholinergic agent. The use of a cholinergic agent, such as carbachol, in combination with a beta-blocker, such as propranolol, produces ventricular asystole at significantly reduced dosages of the cholinergic agent, while maintaining a short half-life and rapid onset of effect.

The cholinergic agent, such as carbachol, is generally administered in an initial intracoronary bolus of about 5 to 150 µg/kg body weight of patient, or about 2 to 20 µg/kg body weight of patient, for example, about 4 to 16 µg/kg, or about 6 to 14 µg/kg, or in one embodiment, about 8 to 12 µg/kg body weight, in a suitable pharmaceutically acceptable carrier or diluent. The bolus infusion of the cholinergic agent is preferably followed by a continuous infusion of the cholinergic agent. The infusion rate is generally about 0.1–4.8 µg/kg body weight patient/min, preferably about 0.1–1.2 µg/kg/min, or about 0.1–1.0 µg/kg/min. A typical total adult dosage of the cholinergic agent, such as carbachol, is about 1 mg to 15 mg for a 120 min period of ventricular asystole. The dosage may be adjusted depending on the surgical procedure. The beta blocker, such as propranolol, is typically administered in a single bolus in a dosage amount of about 0.01 to 0.07 mg/kg body weight of patient, for example about 0.01 to 0.05 mg/kg, or about 0.01 to 0.04 mg/kg. The total amount of propranolol administered is typically about 1 mg to 5 mg, for example about 2 to 4 mg, or about 3 mg.

As described above, the combination of AV node blocking using an effective dosage amount of an AV node blocker (such as carbachol), and/or other means of stimulating the AV node such as vagal nerve stimulation, in combination with an effective dosage amount of a beta blocker (such as propranolol) produces precise and controlled prolonged periods of reversible ventricular asystole of the heart while maintaining the ability of the heart to be electrically paced. Electrical pacing wires are connected to the right ventricle and or left ventricle and are used to pace the heart to maintain the patient's blood circulation during the periods in which the surgeon is temporarily not performing the surgical procedure. Thus, for example, in a CABG procedure, the surgeon can control the pacing of the heart with a convenient foot pedal and can controllably stop the heart as sutures are placed in the vessel walls. The pharmaceutical compositions and methods described above give a surgeon complete control of the beating heart.

For the pharmaceutical compositions described above to be most effective, those pharmaceutical compositions must be precisely delivered to the AV node of the heart upon which they act, preferably by way of the AV nodal branch artery of the heart. New surgical devices and methods are required to allow the surgeon to reliably and easily deliver such pharmaceutical compositions or other drugs or fluids to the heart or other major organ directly via the internal lumen of a coronary vessel. In particular, an intraluminal shunt apparatus is needed which can be easily inserted directly into an incision in a coronary vessel which delivers blood to or drains blood from the AV nodal branch artery, such as the right coronary artery, the posterior descending vein, the left circumflex, or the AV nodal branch artery itself. Direct access to the internal lumen of a vessel via an intraluminal shunt has a number of advantages. First, the intraluminal shunt may be easily employed by the cardiac surgeon under direct or endoscopic visualization without the need for x-ray fluoroscopy, which is often not present in most operating rooms. Moreover, surgeons are not very facile with drug delivery catheters delivered through a percutaneous approach, and the use of an intraluminal shunt obviates the need for a femoral or brachial arterial puncture needed for placement of a drug delivery catheter in a vessel.

Presently, intraluminal shunts are employed by surgeons to reduce intraoperative ischemia and facilitate the construction of coronary artery bypass grafts. For example, the Rivetti-Levinson™ intraluminal shunt (from Heyer-Schulte NeuroCare Group) (patent pending) employs a standard T or L-shaped intraluminal shunt having a main shunt body which is configured to be inserted into a coronary artery vessel and which provides direct or passive perfusion of the distal coronary arterial lumen during construction of coronary bypass grafts in the non-arrested heart. A side port is provided to actively perfuse the coronary artery from a secondary source using a standard luer connection. However, this device is specifically not designed or intended for drug administration into the coronary artery vessel.

U.S. Pat. No. 5,695,504 to Gifford et al. discloses a catheter device for isolating a section of a coronary artery while performing a distal anastomosis. The catheter device includes a T-shaped distal portion which includes a single dedicated blood and/or fluid delivery lumen which allows blood to flow through the device downstream from the anastomosis site. A single side perfusion limb is provided which is in fluid communication with the main perfusion lumen for infusing blood and/or cardioplegia solution into the catheter if the passive blood flow through the main perfusion lumen is insufficient because of a severe stenosis or total occlusion upstream of the anastomosis site.

In light of the foregoing, it is desirable to provide an intraluminal shunt apparatus that can be used to quickly and easily deliver a drug and/or other fluid to the vessel of a patient undergoing a surgical procedure, such as a CABG procedure, while also maintaining either passive or active blood perfusion through the vessel. It would be further desirable to provide such a device that could be used in minimally invasive cardiac surgery procedures (or open-chest surgical procedures) to deliver a pharmaceutical composition to the heart of a patient that is capable of inducing temporary reversible ventricular asystole of the heart while maintaining the ability of the heart to be electrically paced. Preferably, the intraluminal shunt should be configured to be inserted into a target vessel that delivers blood to or drains blood from the AV nodal branch artery of the heart, such as the right coronary artery, the posterior descending vein, the left circumflex, or the AV nodal branch artery itself In this way, the pharmaceutical compositions described above, for example, which act in part on the AV node, can be effectively administered locally to the heart in either a bolus injection or a continuous infusion to provide temporary periods of cardiac standstill.

Further, it would be desirable to provide an intraluminal shunt apparatus which is configured to permit the delivery of the pharmaceutical composition or other fluid in either an anterograde direction (forward direction which is the same direction as normal blood flow through the vessel) or a retrograde direction (reverse direction which is opposite to the direction of normal blood flow through the vessel) through the intraluminal shunt and the coronary vessel. This is particularly important where the surgeon does not have the advantage of x-ray fluoroscopy to precisely position the shunt device at a desired position within a target vessel. Thus, the intraluminal shunt apparatus should provide the surgeon with the capability to deliver the drug or fluid in either an anterograde or retrograde direction depending on whether the shunt apparatus is placed in the target vessel upstream or downstream from the position to which it is desired to deliver the drugs or other fluids.

If would be further desirable to have an intraluminal shunt with sufficient flexibility so that it can be easily inserted into and removed from the target vessel. In addition, the device preferably should also permit mixing of the drug or fluid with the blood perfusing through the device to enhance the effectiveness of the drug or fluid at its target location.

SUMMARY OF THE INVENTION

The present invention involves an intraluminal shunt apparatus for the administration of a drug or fluid into a vessel while also maintaining blood perfusion through the vessel. According to one embodiment, the intraluminal shunt apparatus includes a primary tubular member adapted for insertion into the vessel. The primary tubular member has at least one perfusion lumen defining a perfusion path through the primary tubular member and provides a perfusion path within the vessel.

The primary tubular member may also have an independent fluid delivery lumen extending longitudinally along at least a portion of said primary tubular member. This configuration provides for both a perfusion path through the intraluminal shunt as well as an independent fluid delivery path for the administration of a drug or other fluid. According to one aspect of the invention, the fluid delivery lumen extends between a first discharge port associated with he proximal end of the primary tubular member and a second discharge port associate d with said distal end of the primary tubular member.

In another aspect of the present invention, the intraluminal shunt apparatus may further include at least one secondary tubular member coupled to said primary tubular member. The secondary tubular member may have at least one inner lumen in fluid communication with the independent fluid delivery lumen, thus defining a drug or fluid delivery path independent of the perfusion path.

The outer surface or profile of the primary tubular member is configured to sealingly engage the inside of the vessel into which it is inserted. In one aspect, the outer surface is constructed with an outer diameter or dimension greater than the inside diameter or dimension of the vessel in which it is to be placed. In another aspect, the primary tubular member may include occlusion members extending about the primary tubular member. More specifically, the primary tubular member may include first and second occlusion members spaced apart longitudinally from each other so as to define an occlusion section which is substantially sealed from the blood or other fluids flowing through said perfusion path or said fluid delivery path. In this manner, any incision or opening created in the vessel to facilitate insertion of the primary tubular member is isolated to prevent leakage. In another aspect, the occlusion members may be in the form of flanges, inflatable balloons or sealing cuffs of any number of constructions or materials designed to engage and seal against the vessel wall. To facilitate easy insertion of the primary tubular member into the vessel the proximal and distal ends may be beveled.

According to a further aspect of the present invention, the intraluminal shunt apparatus may include a valve means coupled to the fluid delivery lumen. The valve means allows the drug or fluid to be selectively directed towards either the first discharge port or the second discharge port of the fluid delivery lumen. The valve means may be situated such that it engages and bifurcates the fluid delivery lumen into separate distal and proximal delivery lumen where it may then selectively direct the drug or fluid into either lumen. The valve means may be a one-way valve or more particularly may include a luer connection member rotatably coupled to the secondary tubular member and a tubular rod having an inside lumen extending from the luer connection to a discharge opening which may be positioned within said fluid delivery lumen. Preferably, the valve means is provided at a central portion of the fluid delivery lumen of the primary tubular member.

According to a further aspect of the present invention, a secondary tubular member having first and second independent inner lumen may be coupled to a primary tubular member having first and second independent fluid delivery lumen. The apparatus may be configured such that the first independent fluid delivery lumen, extending longitudinally within the primary tubular member towards the distal end, is in fluid communication with the first independent inner lumen. The second independent fluid delivery lumen, extending longitudinally within said primary tubular member towards said proximal end, is in fluid communication with said second independent inner lumen. The first and second delivery lumen may terminate at distal and proximal discharge ports respectively.

At least one of the first or second independent inner lumens may be fluidly coupled to a drug supply source, for instance one that is adapted to deliver a pharmaceutical composition capable of inducing reversible ventricular asystole in the heart of a patient while maintaining the ability of the heart to be electrically paced. In another aspect, at least one of the first or second independent inner lumens may be fluidly coupled to a source of oxygenated blood such as a radial artery, a femoral artery, the aorta, or a blood perfusion pump circuit.

The intraluminal shunt apparatus of the present invention may be constructed of any suitable biocompatible material such as polyethylene, polyurethane, nylon, silicone, or other suitable single or composite material. Preferably, the material is silicone. In one aspect of the present invention, the primary tubular member and the secondary tubular member are made from different materials. The primary tubular member may be made of a material having a lower hardness than that of the secondary tubular member.

In yet another aspect of the present invention, first and second secondary tubular members are coupled to the primary tubular member. The first and second secondary tubular members each have an independent inner lumen. These inner lumen of the first and second secondary tubular members may be in fluid communication with first and second independent fluid deli very lumen extending longitudinally within the primary tubular member. The secondary tubular members arc generally positioned at an angle relative to the primary tubular member of about 20 to about 90 degrees, preferably about 45 degrees. According to one aspect of the invention, the shunt apparatus may additionally comprise a drug delivery catheter positioned within or through the independent inner lumen. The drug delivery catheter may be manipulated to deliver drugs or other fluids in either a retrograde or an anterograde direction.

In another embodiment t of the present invention, an intraluminal shunt apparatus for the administration of a drug or fluid into a vessel includes a primary tubular member adapted for insertion into a vessel. The primary tubular member has at least one perfusion lumen defining a perfusion path within the vessel through the primary tubular member. According to this embodiment, the shunt apparatus may include a secondary tubular member coupled to the primary tubular member, the secondary tubular member having at least two separate and independent inner lumens, a least one of which may be coupled to the perfusion lumen of the primary tubular member.

In accordance with a further aspect of the present invention, a drug delivery apparatus is provided which includes a primary tubular member sized and dimensioned to be inserted into a vessel, a secondary tubular member fluidly coupled to the primary tubular member and a fluid delivery means for selectively delivering a pharmaceutical composition from the secondary tubular member through the primary tubular member and out either one of the ends of the primary tubular member.

Another aspect of the present invention involves a method for delivering a pharmaceutical composition into a coronary vessel of a patient. The method steps may include providing an intraluminal shunt apparatus having a primary tubular member and a secondary tubular member coupled thereto, preparing an opening in the vessel to permit insertion of the proximal and distal ends of the primary tubular member through the opening, inserting at least the proximal and distal ends of the primary tubular member into the opening in the vessel, and delivering a pharmaceutical composition through the primary tubular member and into the vessel. According to one aspect of the present invention, the pharmaceutical composition is selectively delivered in either an anterograde or a retrograde direction. This may be determined based on the position of the shunt relative to the desired site for drug delivery.

Another embodiment of the present invention may include a kit for conducting a surgical procedure comprising a first container containing a dosage amount of cholinergic receptor agonist, a second container containing a dosage amount of beta blocker, and an intraluminal shunt having a primary tubular member and a secondary tubular member coupled thereto.

The invention described below solves the deficiencies of the prior art and offers a number of other features and advantages that will be apparent to one of ordinary skill in the art from the following detailed description, accompanying figures, and appended claims.

DETAILED DESCRIPTION OF THE INVENTION

The invention will now be described in detail with reference to the accompanying drawings wherein like numerals indicate like elements. Although the invention is not so limited, the detailed description describes the invention in relation to placement of the intraluminal shunt apparatus in a coronary vessel, such as the right coronary artery, during performance of a minimally invasive cardiac surgery procedure, such as a coronary artery bypass graft procedure. The preferred use of the intraluminal shunt apparatus is for the delivery of a pharmaceutical composition into the right coronary artery that is capable of causing reversible ventricular asystole in the heart while maintaining the ability of the heart to be electrically paced. This allows the surgeon to perform the surgical procedure on an arrested (non-beating) heart. However, this example is given by way of illustration only and is in no way meant to be limiting.

Those of ordinary skill in the art will recognize that the present invention can be readily placed in any vessel that supplies blood to or drains blood from any major organ and can be used for any surgical procedure, including other cardiovascular procedures and other medical procedures such as neurosurgery or other vascular surgery procedures. The present invention can be used to deliver any pharmaceutical or diagnostic agent or other fluid into any target vessel depending on the requirements of the particular surgical procedure. Further, in the specific realm of cardiac surgery, the present invention can be used in either closed-chest or open-chest surgical procedures.

For consistency and convenience, throughout the description the two ends of the primary tubular member of the intraluminal shunt apparatus are referred to as the proximal and distal ends respectively, the distal end of the primary tubular member is the end which is to be inserted into the downstream side of the blood vessel and the proximal end being the end which is inserted into the upstream side of the blood vessel.

Figure 1:
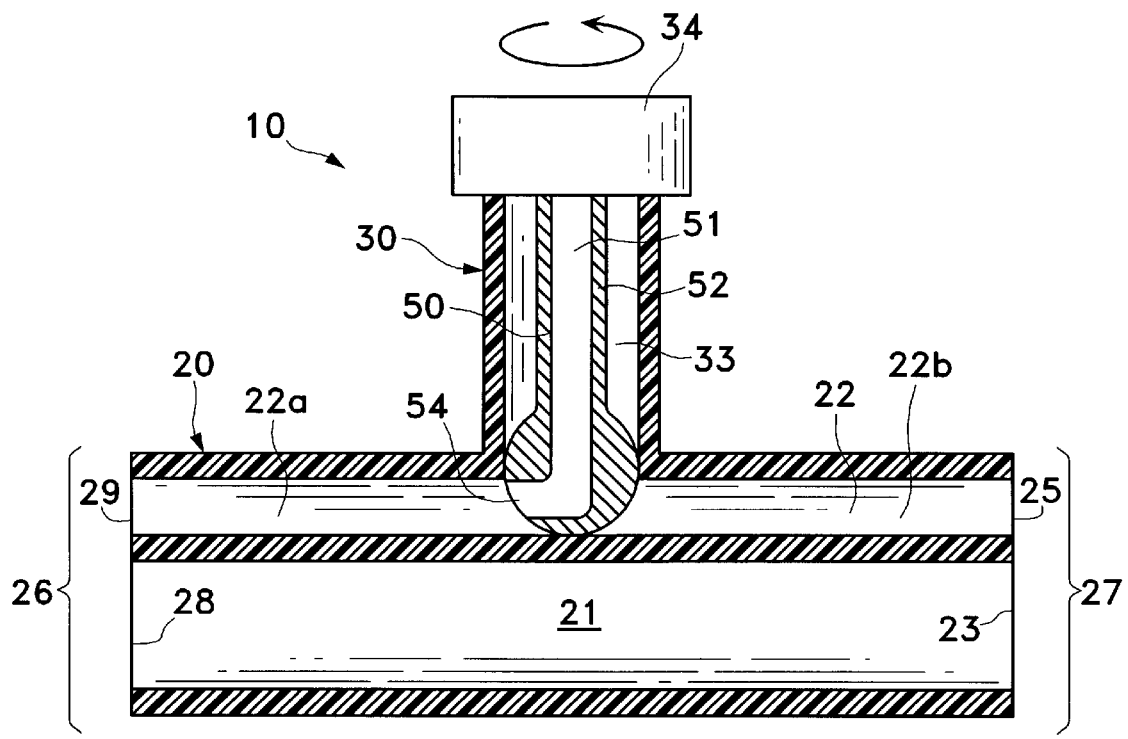
FIG. 1 is a cross-sectional view of a preferred embodiment of an intraluminal shunt apparatus of the present invention.
Figure 1A:
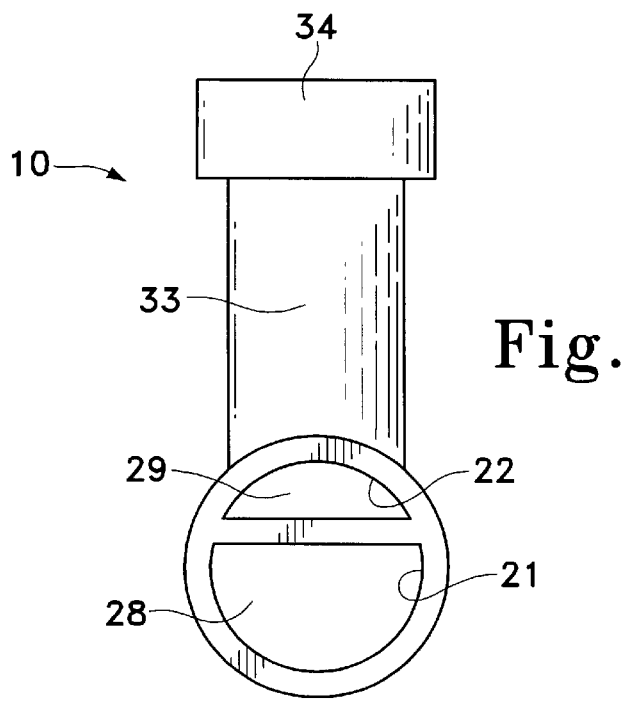
FIG. 1a is an end view of the intraluminal shunt apparatus of FIG. 1.
Figure 2:
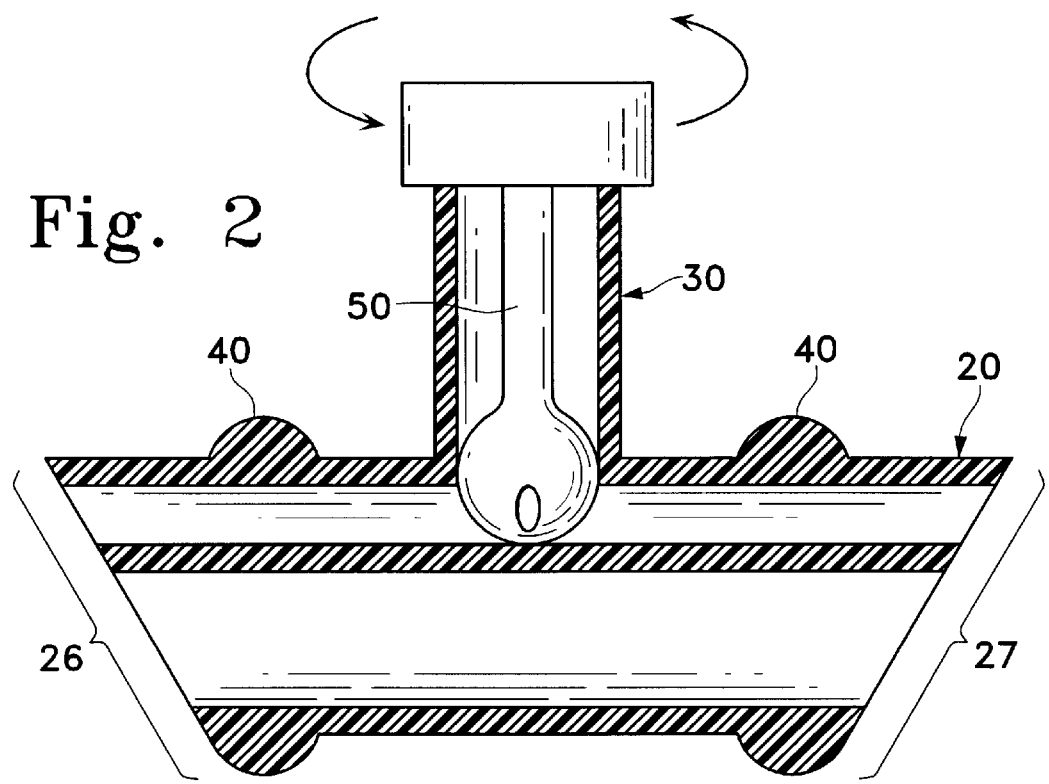
FIG. 2 is a side cross-sectional view of an alternative construction of the intraluminal shunt apparatus of FIG. 1.

Referring to FIGS. 1–2, a first preferred embodiment of an intraluminal shunt apparatus constructed in accordance with the present invention is shown. The illustrated intraluminal shunt apparatus s generally referred to as reference numeral 10. Intraluminal shunt 10 can be constructed of any suitable biocompatible material which provides sufficient flexibility to facilitate insertion of the shunt apparatus into the target vessel. Moreover, this material is sufficiently rigid to maintain its shape within the target vessel to allow for safe and efficient blood flow through the apparatus 10. Suitable materials include polyethylene, polyurethane, nylon, or silicone, preferably silicone. The intraluminal shunt apparatus may also be made of composite or reinforced materials such as certain self expanding stent supported materials.

The intraluminal shunt apparatus 10 comprises a primary tubular member 20 which has a proximal end 26 and a distal end 27, respectively. As seen in FIG. 2, the proximal and distal ends 26, 27 optionally have a beveled configuration to facilitate insertion of the primary tubular member 20 into the target vessel. Preferably, the proximal and distal ends 26, 27 are beveled at an angle of about 30 to about 60 degrees relative to the longitudinal axis of the primary tubular member 20, and most preferably are beveled at an angle between about 30 degrees to about 60 degrees, preferably about 45 degrees.

The primary tubular member 20 includes an inner blood perfusion lumen 21 which extends longitudinally between a proximal blood perfusion port 28 and a distal blood perfusion port 23 (see FIG. 1). Blood perfusion lumen 21 allows the flow of blood through the primary tubular member to thereby reduce intra-operative ischemia downstream of the vessel during use of the device.

The primary tubular member 20 also includes at least one inner fluid delivery lumen 22 which extends between proximal discharge port 29 and a distal discharge port 25 (see FIG. 1). Preferably, inner fluid delivery lumen 22 is separate and independent from inner perfusion lumen 21. The fluid delivery lumen 22 extends longitudinally along at least a portion of primary tubular member 20, but need not extend the entire axial length of the primary tubular member as shown. For example, the fluid delivery lumen can terminate at a discharge port short of the proximal and distal ends of the primary tubular member 22 to permit mixing of a drug or fluid with blood perfusing through the device (see, e.g., FIG. 4b). Additionally, the fluid delivery lumen 22 can include one or more side perfusion ports or openings (not shown) which will enhance mixing of the drug or fluid with blood perfusing through the device.

The sizes and cross-sectional shapes of primary tubular member 20 and its respective separate blood perfusion and fluid delivery lumens 21, 22 may vary depending on the size of the target vessel into which they are inserted, and generally are selected to provide optimum blood perfusion and/or drug delivery through the target vessel. The primary tubular member 20 is of sufficient outside diameter to fit securely within the interior walls of the target vessel into which it is placed, and preferably has an outside diameter of between about 1.0 to about 6.0 mm, and most preferably about 1.0 to about 4.0 mm. The primary tubular member 20 preferably has a length of between about 1.0 to about 5.0 cm, and most preferably about 3.0 cm.

Blood perfusion lumen 21 and fluid delivery lumen 22 can have any one of a number of cross-sectional configurations as would be obvious to one of ordinary skill in the art, such as a circular, oval, crescent-shaped, or D-shaped configurations, or any other configuration including coaxial arrangements. The total combined fluid flow surface area through lumens 21 and 22 can also vary depending on the application of the device, and generally will range from between about 0.50 mm$^2$ and 30.0 mm$^2$.

Figure 2A:
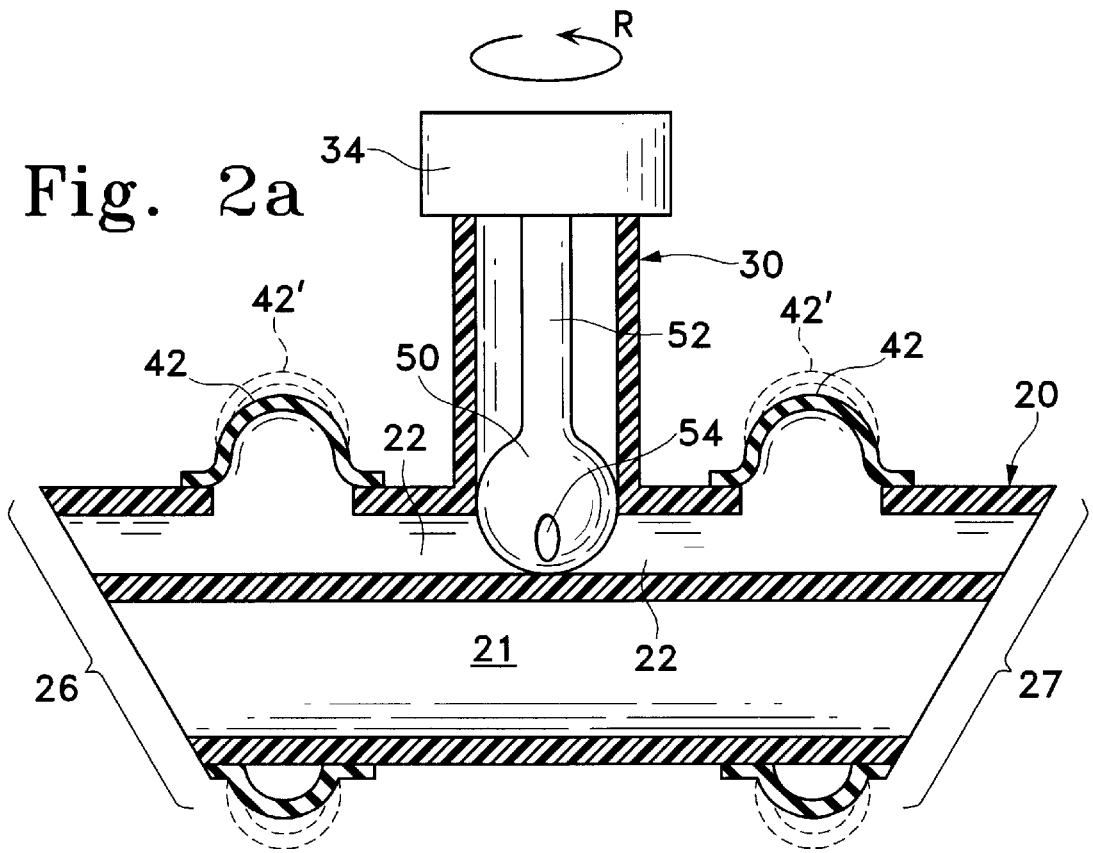
FIG. 2a is a side cross-sectional view of an alternative construction of the intraluminal shunt apparatus of FIG. 1.

The outer surface or profile of primary tubular member 20 may optionally be constructed to seal against the inside of the vessel wall. This may be accomplished by configuring the primary tubular member to have an outside diameter or profile that is larger than the inside diameter of the intended vessel. Optionally, as shown in FIG. 2, the primary tubular member can be provided with a pair of sealing cuffs or flanges 40 which extend about the primary tubular member close to proximal and distal ends 26, 27, respectively. Flanges 40 are constructed of any suitable biocompatible material, preferably silicone. Flanges 40 help to secure the primary tubular member in the vessel during use of the device 10 and to seal the vessel to force blood through the device. Further optionally, as seen in FIG. 2a, flanges 40 may be replaced by a pair of inflatable low-pressure balloons 42 which each have an interior which is in fluid communication with fluid delivery lumen 22. The flow of blood, drugs, or any other fluid through fluid delivery lumen 22 will cause either of the balloons to inflate to engage the inner wall of the target vessel, as seen in phantom by reference numeral 42'. The low-pressure balloons 42 have the advantage of allowing the intraluminal shunt apparatus 10 to expand to effectively fit the size of the particular vessel into which the apparatus is inserted.

The intraluminal shunt apparatus 10 further comprises a secondary tubular member 30 which terminates distally at a female luer connection member 34. Female luer connection member 34 is rotatably coupled to secondary tubular member 30. The secondary tubular member 30 includes an inner lumen 33 which is in fluid communication with fluid delivery lumen 22 of the primary tubular member 20. The cross-sectional shape and sizing of secondary tubular member 30 and inner lumen 33 is selected to provide optimum fluid flow for drugs or other fluids through the shunt apparatus 10. Typically, the total surface area of perfusion lumen 33 will be substantially equal to the surface area of fluid delivery lumen 22, and will vary from between about 0.50 mm$^2$ and 30.0 mm$^2$. Inner lumen 33 can have any general cross-sectional configuration as described above for blood perfusion lumen 21 and fluid delivery lumen 22, such as a circular, oval, crescent-shaped, or D-shaped configuration, for example.

Any standard cannula or catheter connected to a drug supply source (not shown) with a male luer tip can be connected to the luer connection member 34 of the secondary tubular member 30 to administer a drug or fluid into the target vessel. If necessary. supplemental blood flow can also be delivered by connecting the luer connection member 34 to any source of arterialized blood, such as a radial artery, femoral artery, aorta, or a blood perfusion pump circuit.

In a preferred embodiment, the intraluminal shunt is provided with a fluid directing member for selectively directing drugs or other fluids towards either the proximal or distal end of the device. For example, the fluid directing member may be a valve means. Any suitable valve member may be used which allows selection between the desired retrograde and anterograde flow paths including ball valves, spool valves, poppet valves, diaphram valves, gate valves, or the like. In one embodiment shown in FIG. 1, a one-way valve member 50 is provided which is adapted to permit a drug or other fluid to flow and be administered from either the proximal end 26 or the distal end 27 of the primary tubular member of the shunt apparatus. With this configuration, the intraluminal shunt can delivery drugs and/or other fluids in either an anterograde or retrograde direction through the primary tubular member 20, as will be described in greater detail hereinafter. Valve member 50 bifurcates fluid delivery lumen 22 into a retrograde lumen portion 22a and an anterograde lumen portion 22b. The valve member 50 preferably includes a tubular fillet rod 52 which is integrally connected to luer connection member 34 at its proximal end. Fillet rod 52 defines an inner lumen 51 therewithin which fluidly communicates with at least one discharge opening 54 at a distal end of the rod 52.

The cross-sectional dimensions of fillet rod 52 preferably are substantially the same as the cross-sectional dimensions of fluid delivery lumen 22 so that the distal end of fillet rod 52 substantially seals fluid delivery lumen 22. Thus, by rotating female luer connection member 34 about a vertical axis along the length of the secondary tubular member 30, discharge opening 54 can be rotated to be in fluid communication with either fluid delivery lumen portion 22a or 22b. Discharge opening 54 is shown in fluid communication with fluid delivery lumen 22a in FIG. 1, and is shown for clarity rotated to a neutral position in the various other figures. This will also effectively seal off the other fluid delivery lumen portion 22b, 22a from fluid flow through that portion. In this way, a drug or fluid can be directed through female luer connection member 34 in either an anterograde or a retrograde direction. A marking such as an arrow or colored line (not shown) can be provided on luer connection member 34 to indicate the position of the discharge opening 54 in relation to the primary tubular member 20.

Figure 2B:
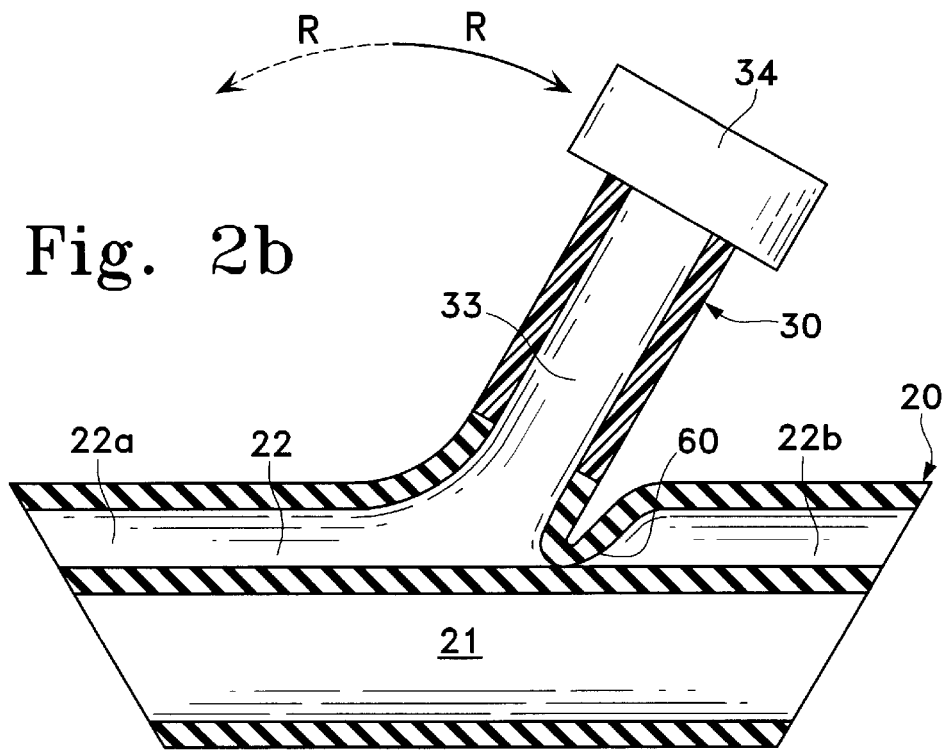
FIG. 2b is a side cross-sectional view of an alternative construction of the intraluminal shunt apparatus of FIG. 1.

An alternative embodiment of a valve means is shown in FIG. 2b. The valving action in this embodiment is created by forcing the secondary tubular member 30 radially laterally towards either the proximal or distal end of the primary tubular member 20 in the direction "R" as shown in FIG. 2b. This will cause a portion 60 of the fluid delivery lumen 22 to crimp or fold in on itself to thereby substantially seal off one of the fluid delivery lumen portions 22a, 22b. Preferably, the secondary tubular member 30 and the primary tubular member 20 in this embodiment are made of varying durometer silicone materials, wherein the durometer hardness of the material of the secondary tubular member 30 is greater than the durometer hardness of the material of the primary tubular member 20. This will facilitate the crimping action of the primary tubular member 20 as the secondary tubular member 30 is moved laterally proximally or distally in relation to the primary tubular member. In addition, a separate drug delivery catheter or cannula (not shown) can easily be inserted into the secondary tubular member and, without kinking, can be used to deliver a drug or fluid in the non-sealed direction through the primary tubular member 20.

Figure 3:
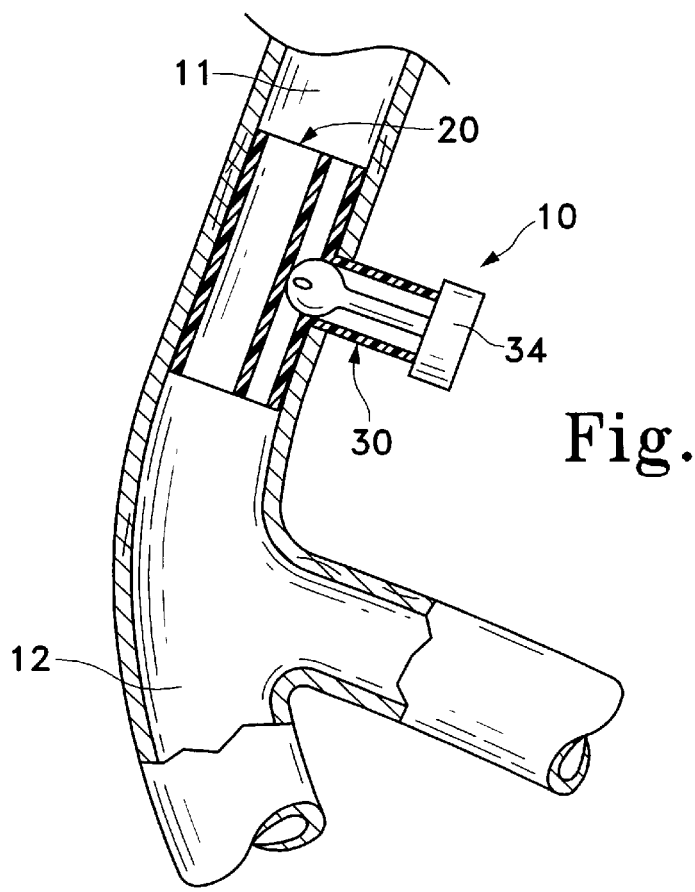
FIG. 3 is a side cross-sectional view of the intraluminal shunt apparatus of FIG. 1 shown inserted into the right coronary artery of a patient.

The inventive method of administering a drug or fluid into a patient while maintaining perfusion is described below with respect to a minimally invasive cardiac surgical procedure such as a CABG procedure as described with reference to FIG. 3. As noted above, this particular preferred method is for illustration purposes only and is in no way intended to limit the invention to its use in the minimally invasive cardiac surgical procedure described below. The present invention can be readily placed in any vessel, especially those that supplies blood to or drains blood from any major organ and can be used for any surgical procedure such as a neurosurgery or other vascular surgery procedure. The present invention can be used to deliver any pharmaceutical or diagnostic agent blood, or other fluid into any target vessel depending on the requirements of the particular surgical procedure. Further, the invention can be used for closed-chest or open-chest surgical procedures.

Minimally invasive direct CABG, like any other operation requires adequate access to the heart prior to placement of the shunt apparatus 10. Different methods of access can be used by the surgeon to expose the heart such as an anterior left/right thoracotomy, a partial or median sternotomy, a parasternal thoracotomy, and an upper midline incision. Most preferably, a 6 to 8 cm left thoracotomy incision is used to access the heart. With the heart so exposed, an incision is made in the right coronary artery 11 or other target vessel at the desired drug delivery site, preferably near the junction to the posterior descending artery 12. After preparing the incision or opening, an intraluminal shunt device having a perfusion lumen and at least one side delivery lumen is inserted through the incision. In a preferred embodiment, a shunt apparatus as those described herein is provided and both the proximal end 26 and the distal end 27 of the primary tubular member 20 are introduced into the right coronary artery 11 through the incision. The proximal end 26 of the primary tubular member 20 is positioned upstream of the incision site and the distal end 27 of the primary tubular member 20 is positioned downstream of the incision site. The optional flanges 40 firmly position the primary tubular member 20 within the internal walls of the right coronary artery 11 and seal the vessel to maximize blood perfusion through it.

A drug or fluid is then delivered through a cannula or catheter having a male luer connector (not shown) connected to luer connector 34 of secondary tubular member 30. Preferably, the drug comprises a pharmaceutical composition which is capable of inducing precise and controlled periods of reversible ventricular asystole of the heart while maintaining the ability of the heart to be electrically paced. Preferably, the pharmaceutical composition comprises a combination of an AV node blocker and a beta blocker. The beta blocker is preferably provided in an amount sufficient to substantially reduce the amount of AV node blocker required to induce ventricular asystole. For example, the AV node blocker may be present in the composition in an amount which is 50% or less by weight, or optionally about 1 to about 20% by weight of the amount of AV node blocker alone required to induce ventricular asystole.

The pharmaceutical composition such as an AV node blocker, capable of causing ventricular asystole in a preferred embodiment is a cholingeric agent such as carbachol, although other cholingeric agents may be used as well. In the preferred embodiment, the beta blocker is propranolol, although other suitable beta blockers may be used as well. The administration of the beta blocker is preferably prior to, or contemporaneously with, the administration of the cholinergic agent, and results in a synergistic effect between the beta blocker and the cholinergic agent. The use of a cholinergic agent, such as carbachol, in combination with a beta-blocker, such as propranolol, produces ventricular asystole at significantly reduced dosages of the cholinergic agent, while maintaining a short half-life and rapid onset of effect.

The cholinergic agent, such as carbachol, is generally administered in an initial intracoronary bolus of about 5 to 150 $\mu$g/kg body weight of patient, or about 2 to 20 $\mu$g/kg body weight of patient, for example, about 4 to 16 $\mu$g/kg, or about 6 to 14 $\mu$g/kg, or in one embodiment, about 8 to 12 $\mu$g/kg body weight, in a suitable pharmaceutically acceptable carrier or diluent. The bolus infusion of the cholinergic agent is preferably followed by a continuous infusion of the cholinergic agent. The infusion rate is generally about 0.1–4.8 $\mu$g/kg body weight patient/min, preferably about 0.1–1.2 $\mu$g/kg/min, or about 0.1–1.0 $\mu$g/kg/min. A typical total adult dosage of the cholinergic agent, such as carbachol, is about 1 mg to 15 mg for a 120 min period of ventricular asystole. The dosage may be adjusted depending on the surgical procedure. The beta blocker, such as propranolol, is typically administered in a single bolus in a dosage amount of about 0.01 to 0.07 mg/kg body weight of patient, for example 0.01 to 0.05 mg/kg, or about 0.01 to 0.04 mg/kg. The total amount of propranolol administered is typically about 1 mg to 5 mg, for example about 2 to 4 mg, or about 3 mg.

As described above, the combination of AV node blocking using an effective dosage amount of an AV node blocker (such as carbachol), and/or other means of stimulating the AV node such as vagal nerve stimulation, in combination with an effective dosage amount of a beta blocker (such as propranolol) produces precise and controlled prolonged periods of reversible ventricular asystole of the heart while maintaining the ability of the heart to be electrically paced.

Depending on the relative position of the AV nodal branch artery in relation to the incision site in the target vessel 11, the surgeon can manipulate valve member 50 so that the pharmaceutical composition can be delivered in either an anterograde or a retrograde direction through the primary tubular member 20. To determine the most effective route of administration, the surgeon can deliver a small amount of drug in both the anterograde and retrograde direction. Once the appropriate drug delivery direction is determined, the drug can be continuously delivered in that direction to produce controlled periods of cardiac standstill. Moreover, if necessary, continuous drug infusion can be interrupted and supplemental blood flow can be provided in the anterograde direction by connecting the luer connector member 34 to an appropriate source of oxygenated blood such as a radial artery, femoral artery, aorta, or blood pump perfusion circuit, or any other suitable blood supply.

Electrical pacing wires are connected to the right ventricle and or left ventricle and are used to pace the heart to maintain the patient's blood circulation during the periods in which the surgeon is not performing the surgical procedure. Thus, for example, in a coronary artery bypass graft procedure (such as a left interior thoracic artery (LITA) to left anterior descending artery (LAD) anastomosis), the surgeon can control the pacing of the heart with a convenient foot pedal and can controllably stop the heart as sutures are placed in the vessel walls. When the coronary artery bypass graft procedure is complete, the intraluminal shunt apparatus 10 can be removed by applying gentle pressure on the secondary tubular member 30 and then removing the primary tubular member 20 from the incision.

Figure 4:
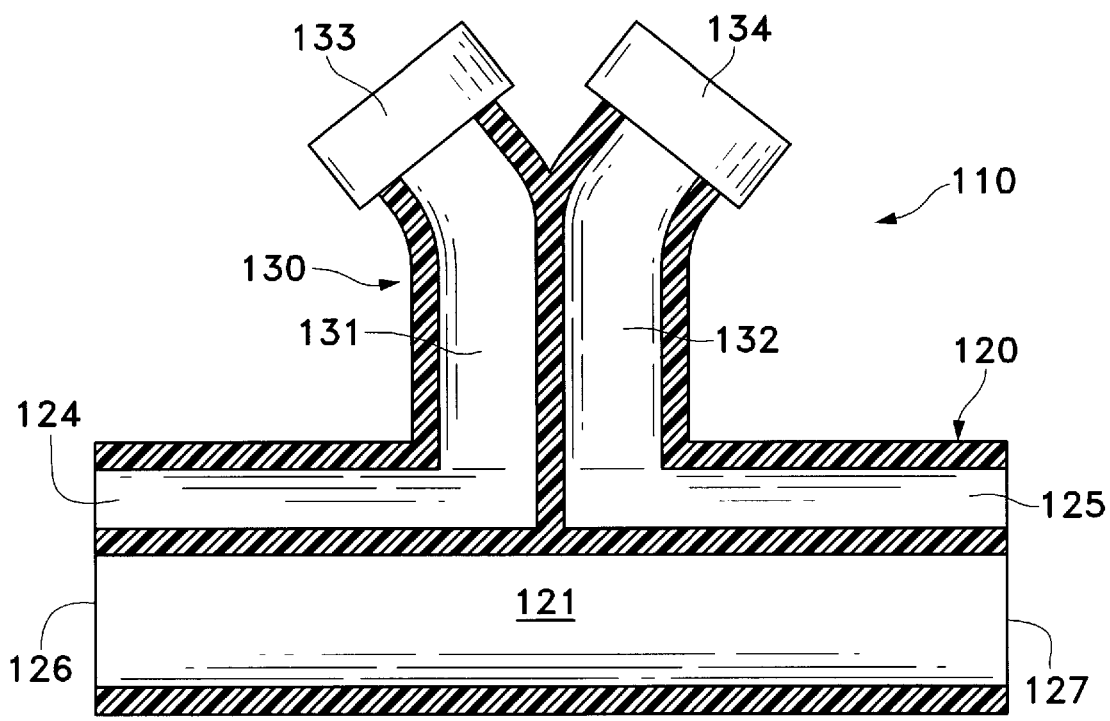
FIG. 4 is a side cross-sectional view of an alternative construction of the intraluminal shunt apparatus of FIG. 1.

An alternative embodiment of the intraluminal shunt apparatus of FIG. 1 is shown in FIG. 4. In this intraluminal shunt apparatus 110, the valve member 50 of the intraluminal shunt apparatus of FIG. 1 is replaced with two dedicated, separate and independent fluid delivery lumens 124 and 125, respectively. Retrograde fluid delivery lumen 124 extends within the primary tubular member 120 from a discharge port (not shown) in the proximal end 126 of the primary tubular member 120 to a location in the central portion of the primary tubular member. Anterograde fluid delivery lumen 125 extends within the primary tubular member 120 from a discharge port (not shown) in the distal end 127 of the primary tubular member to a location adjacent retrograde fluid delivery lumen 124. Inner blood perfusion lumen 121 within primary tubular member 120 is similar to blood perfusion lumen 21 of FIG. 1.

A secondary tubular member 130 comprises first 13 1 and second 132 inner lumens which extend within the secondary tubular member 130. First inner lumen 131 is fluidly coupled to retrograde fluid delivery lumen 124 at one end, and to a female luer connection member 133 at its other end. Second inner lumen 132 is fluidly coupled to anterograde fluid delivery lumen 125 at one end, and to a female luer connection member 134 at its other end. A male luer tip can be used for connecting female luer connection members 133, 134 connected to respective lumens 131 or 132 to a drug or fluid supply source (not shown) for administering a drug or fluid into the vasculature circulation in either an anterograde or retrograde direction. Moreover, supplemental blood flow can also be delivered in the anterograde direction by connecting the luer connection member 133 to any source of arterialized blood, such as a radial artery, femoral artery, aorta or a blood perfusion pump circuit.

Figure 4A:
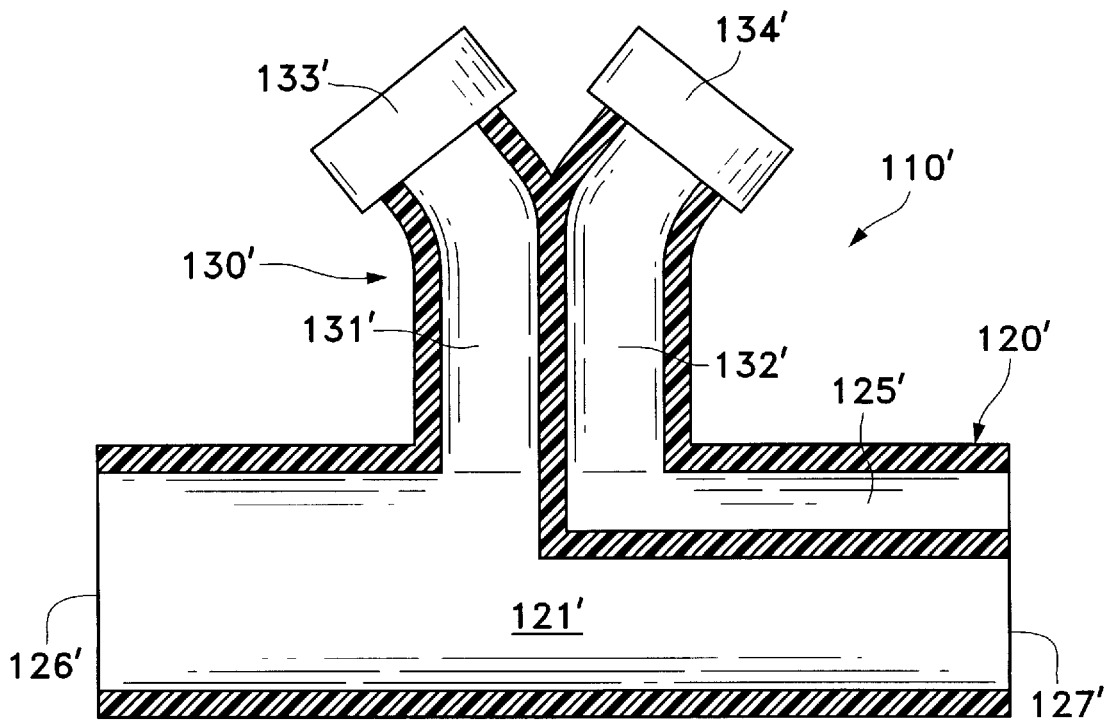
FIG. 4a is a side cross-sectional view of an alternative construction of the intraluminal shunt apparatus of FIG. 4.

FIG. 4a depicts an alternative configuration for the primary tubular member 120 of FIG. 4, in which the modified primary tubular member 120' only includes a single fluid delivery lumen 125'. Fluid delivery lumen 125' extends partially within the primary tubular member 120' from a discharge port (not shown) in the distal end 127' of primary tubular member 120' to a location in the central portion of primary tubular member 120'. Inner lumen 132' of secondary tubular member 130' is fluidly coupled to fluid delivery lumen portion 125', while inner lumen 131' of secondary tubular member 130' is in fluid communication with blood perfusion lumen 121'. The primary tubular member 120' of this embodiment can be inserted into the target vessel with fluid delivery lumen 125' directed in either the anterograde direction of FIG. 4a, or in a retrograde direction (not shown) for delivery of a drug or fluid upstream of the incision site. An appropriate marker (not shown) can be provided on the primary tubular member 120' to indicate in which direction the fluid delivery lumen 125' is pointing. A particular advantage of this embodiment is that where it is appropriate to administer a drug or fluid in an anterograde direction through primary tubular member 120' (i.e., where the device 110' is placed upstream of the AV nodal branch artery), the drug or fluid can be administered via lumen 131' (as well as lumen 132'). Delivery of the drug or fluid through lumen 131' is advantageous because it permits mixing of the drug or fluid with the blood within blood perfusion lumen 121' prior to the blood perfusing distally of the primary tubular member 120'. This can enhance the effectiveness of the pharmaceutical compositions described above because it will increase the likelihood that a greater percentage amount of those compositions reach the AV nodal branch artery via the normal blood circulation through the vessel, rather than overshooting the AV nodal branch artery. Moreover, supplemental blood flow can also be delivered simultaneously in the anterograde direction by connecting the luer connection member 134' to any source of arterialized blood, such as a radial artery, femoral artery, aorta, or a blood perfusion pump circuit. Where it is necessary to deliver the drug or fluid in the retrograde direction (i.e., where the incision site in the target vessel is downstream from the AV nodal branch artery), the primary tubular member 120' can be inserted into the vessel such that the fluid delivery lumen 125' is pointed in the retrograde direction. The drug or fluid can then be administered in a retrograde fashion through the fluid delivery lumen 125', while simultaneous supplemental blood flow can be provided into the blood perfusion lumen 121' via inner lumen 131', if required.

Figure 4B:
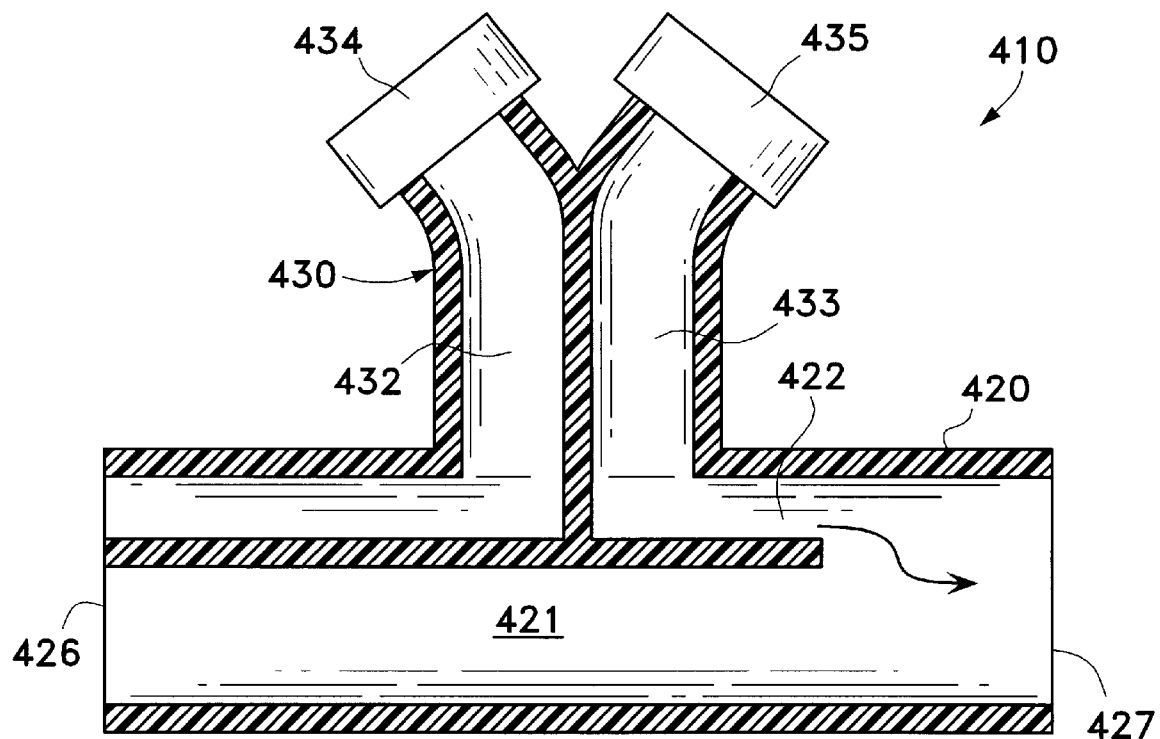
FIG. 4b is a side cross-sectional view of an alternative construction of the intraluminal shunt apparatus of FIG. 1.

A further alternative embodiment of the intraluminal shunt apparatus of FIG. 1 is shown in FIG. 4b. The device of FIG. 4b is designed to enhance the mixing of a drug or other fluid with the blood perfusing distally through the device to enhance the effectiveness of the drug or other fluid at its target location. The intraluminal shunt apparatus 410 of FIG. 4b includes a primary tubular member 420 which has a blood perfusion lumen 421 extending from a port in the proximal 426 and distal end 427 of the primary tubular member 420. The primary tubular member also includes at least one inner fluid delivery lumen 422 which extends only partially along the axial length of the primary tubular member 420. Fluid delivery lumen 422 can include one or more side openings or ports (not shown). A secondary tubular member 430 is coupled to primary tubular member 420 and includes a first inner lumen 432 which is fluidly coupled to blood perfusion lumen 421 at its distal end, and a second inner lumen 433 which is fluidly coupled to fluid delivery lumen 422 at its distal end. First and second inner lumens 432, 433 are each coupled to respective female luer connection members 434, 435 at a proximal end of the secondary tubular member 430. A drug or other fluid can be administered via inner lumen 433 (or inner lumen 432) of secondary tubular member 430 and will mix with the blood perfusing distally of the device 410 prior to exiting from the primary tubular member 420. This mixing of the drug or fluid with the blood will enhance the effectiveness of the drug or fluid at its target location since it will ensure that a greater percentage amount of the drug or fluid reaches its desired target, and does not bypass the target location due to a potential jetting effect.

Figure 5:
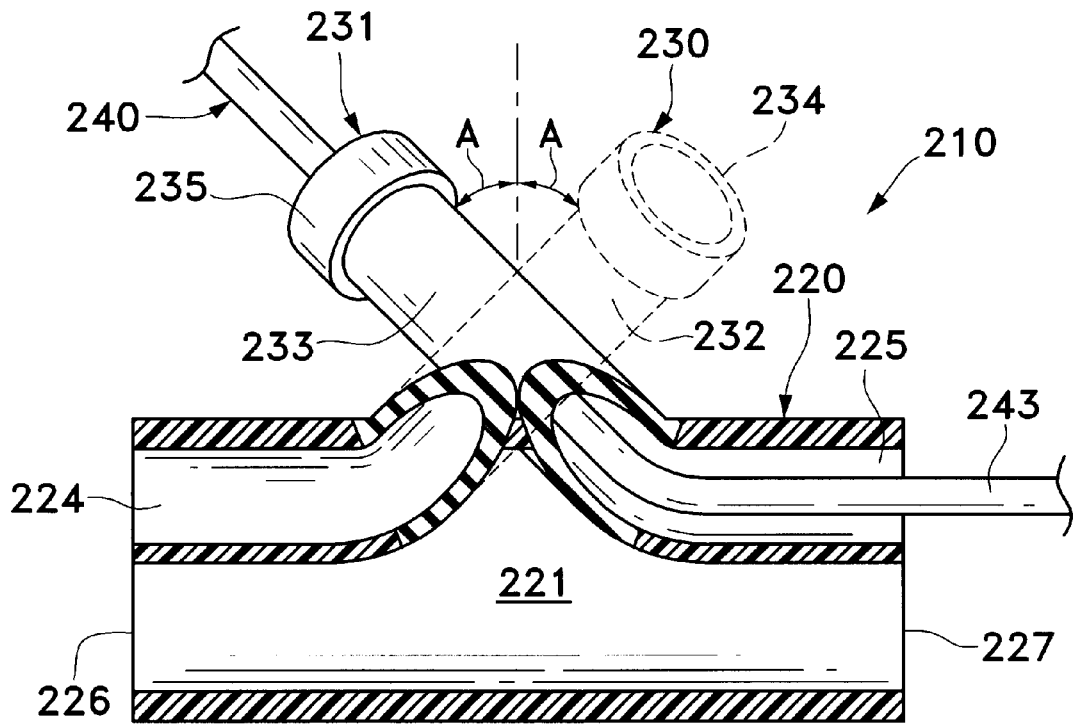
FIG. 5 is a side cross-sectional view of an alternative construction of the intraluminal shunt apparatus of FIG. 1.
Figure 5A:
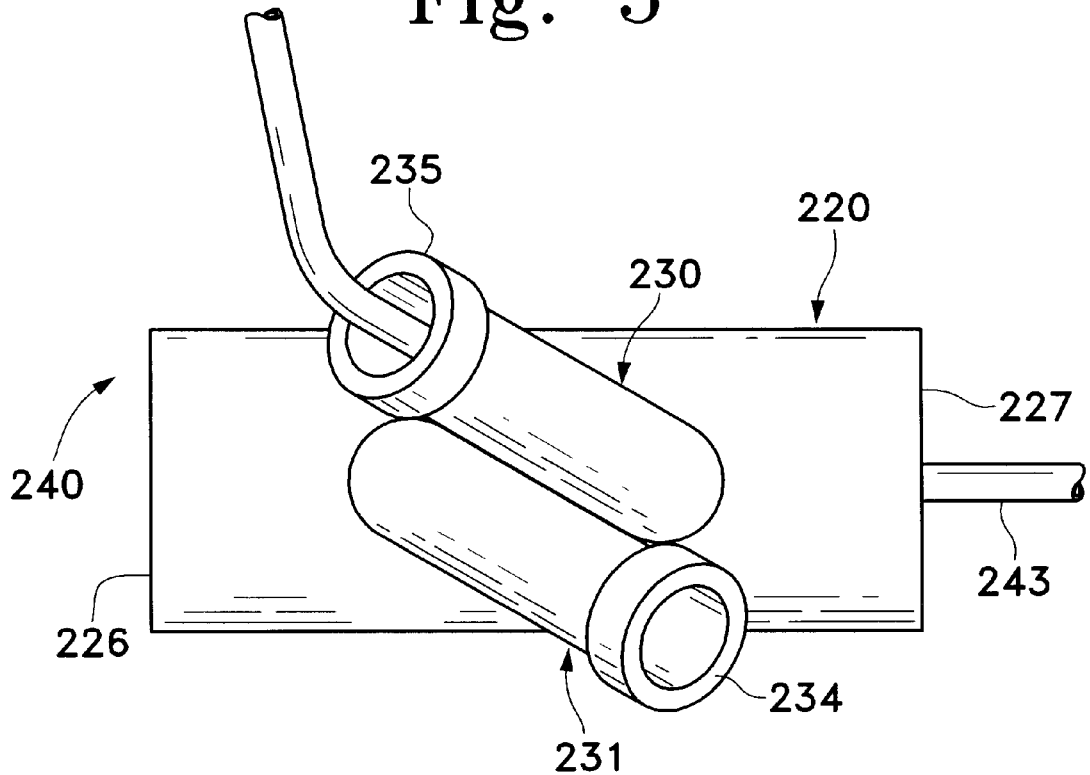
FIG. 5a is top view of the intraluminal shunt apparatus of FIG. 5.

A further alternative embodiment of the intraluminal shunt apparatus of FIG. 1 is shown in FIG. 5. Similar to FIG.

4, in the intraluminal shunt apparatus 210 of FIG. 5, the primary tubular member 220 includes two dedicated, separate and independent fluid delivery lumens 224, 225, respectively. Retrograde fluid delivery lumen 224 extends within the primary tubular member 220 from a discharge port (not shown) in the proximal end 226 of the primary tubular member 220 to a location in the central portion of the primary tubular member. Anterograde fluid delivery lumen 225 extends within the primary tubular member 220 from a discharge port (not shown) in the distal end 227 of the primary tubular member to a location near retrograde fluid delivery lumen 224. Two secondary tubular members 230, 231 are provided which each include a separate inner lumen 232. 233, respectively. Preferably, secondary tubular members 230, 231 are spaced apart from one another and are each displaced at an angle "A" with respect to a line transverse to an axial length of primary tubular member 220, the angle "A" preferably being between 30 and 60 degrees. Inner lumen 232 of secondary tubular member 230 is fluidly coupled to retrograde fluid delivery lumen 224 at one end, and to a female luer connection member 234 at its other end. Inner lumen 233 of secondary tubular member 231 is fluidly coupled to anterograde fluid delivery lumen 225 at one end, and to a female luer connection member 235 at its other end. A male luer tip (not shown) can be used for connecting either lumen 232 or lumen 233 of the secondary tubular members 230, 231 to a drug or fluid supply source (not shown) for administering a drug of fluid into the blood circulation in either an anterograde or a retrograde direction, as required. Moreover, supplemental blood flow can also be delivered in the anterograde direction by connecting the luer connection member 235 to any source of arterialized blood, such as a radial artery, femoral artery, aorta, or a blood perfusion pump circuit.

Additionally, inner lumens 232, 233 of respective secondary tubular members 230, 231 are preferably both sized to permit insertion of a drug delivery catheter 240 into and through the lumens. Drug delivery catheter 240 preferably is a small diameter (for example, about 1 to 4 French) single lumen catheter with at least one drug delivery opening (not shown) located at a distal end 243 of the catheter to provide selective coronary artery drug delivery. Drug delivery catheter 240 has a sufficient length and flexibility to extend transluminally through the intraluminal shunt apparatus 210 such that its proximal end (not shown) is external to either secondary tubular member 230 or 231 and its distal end portion 243 is external to the respective proximal or distal end 226, 227 of the primary tubular member 220. Drug delivery catheter 240 allows the administration of a drug or fluid remote from the intraluminal shunt apparatus 210, if such delivery is required. This drug delivery approach advantageously allows the drug or fluid to be delivered more locally to the AV nodal branch artery, if necessary. A standard sealing adapter such as a Touhy-Bourst (not shown) can be connected to the respective luer connection members 234, 235 to prevent the backflow of drugs, blood, or other fluids through respective lumens 232, 233.

Figure 6:
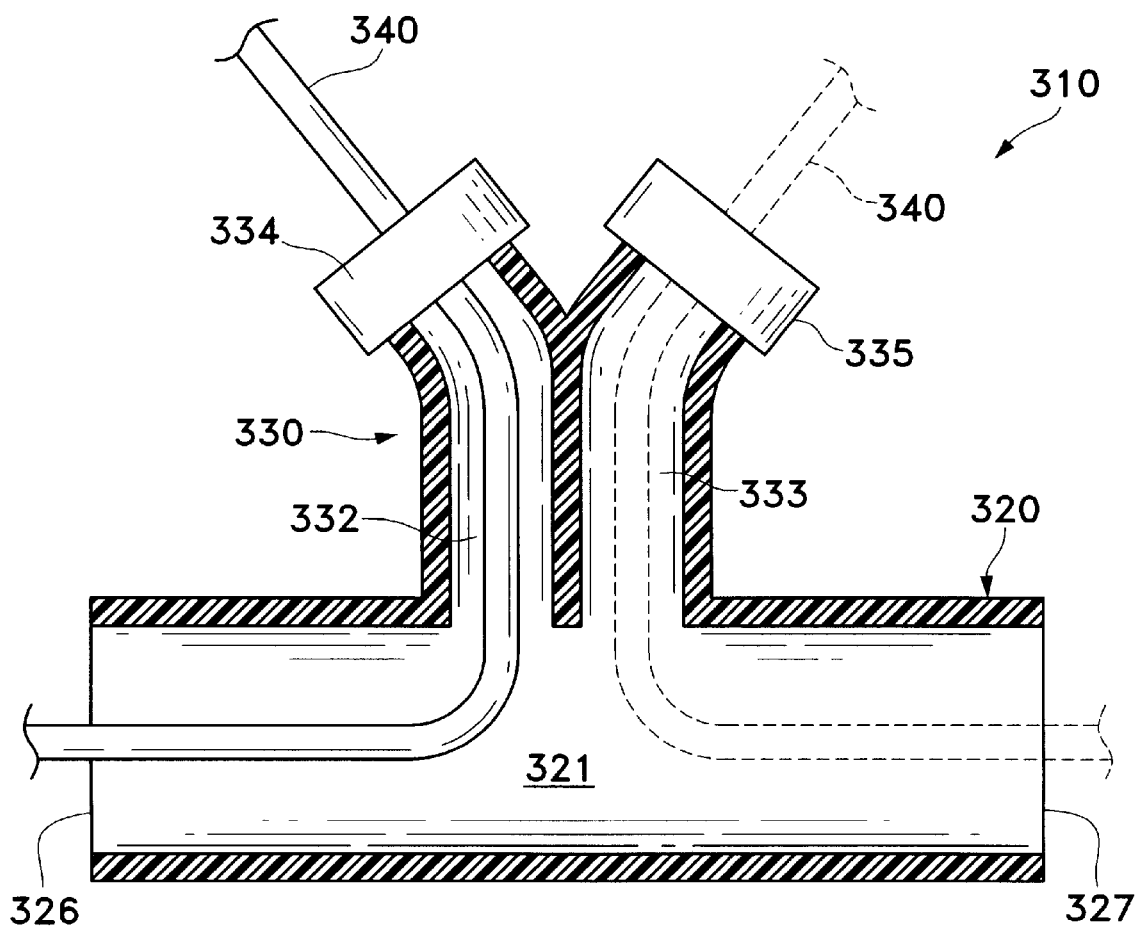
FIG. 6 is a side cross-sectional view of an alternative embodiment of the intraluminal shunt apparatus of FIG. 1.

Because the use of a separate drug delivery catheter 240 gives a surgeon more flexibility and control over the location of the delivery of a drug or fluid into the target vessel, it may not be necessary to provide separate fluid delivery and blood perfusion lumens within the primary tubular member. Thus, for example, in the alternative embodiment of FIG. 6, the primary tubular member 320 of shunt 310 includes only a single inner blood perfusion lumen 321 which extends within the primary tubular member 320 between a perfusion port (not shown) in the proximal and distal ends 326, 327 of the primary tubular member. The secondary tubular member 330 in this embodiment includes two separate and independent inner lumens 332, 333, respectively, which are each in fluid communication with blood perfusion lumen 321. Alternatively, without departing from the scope of the invention, the intraluminal shunt apparatus can comprise two separate and independent secondary tubular members which each have an inner lumen therewithin which is fluidly coupled to blood perfusion lumen 321. At least one of the inner lumens 332, 333 is sized to permit insertion of drug delivery catheter 340 into and through the lumen. The drug delivery catheter 340 preferably has a sufficiently small diameter so as not to substantially impede the flow of blood through the blood perfusion lumen 321. Drug delivery catheter 340 can be inserted into either lumen 332 or lumen 333 by the surgeon to deliver a drug or fluid in either a retrograde or anterograde fashion, as required. If necessary, simultaneous supplemental blood flow can also be delivered to the vessel via blood perfusion lumen 321 by connecting the luer connection member 335, 334 of the other, unused inner lumen 333, 332 of secondary tubular member 330 to any source of arterialized blood, such as a radial artery, femoral artery, aorta, or a blood perfusion pump circuit. A standard sealing adapter such as a Touhy-Bourst (not shown) can be connected to the respective luer connection members 334, 335 to prevent the backflow of drugs, blood, or other fluids through respective lumens 332, 333.

While the above is a complete description of the preferred embodiments of the present invention, various alternatives, modifications and equivalents may be used. Therefore, the above description should not be taken as limiting the scope of the invention, which is defined by the following claims.

What is claimed is:

1. An intraluminal shunt apparatus for administration of fluid into a vessel while maintaining blood perfusion through the vessel, said apparatus comprising:

a primary tubular member adapted for insertion into said vessel, said primary tubular member having a proximal end and a distal end;

at least one blood perfusion lumen defining a perfusion path through the primary tubular member;

at least one independent fluid delivery lumen extending longitudinally along at least a portion of said primary tubular member;

at least one secondary tubular member coupled to said primary tubular member, said secondary tubular member having at least one inner lumen in fluid communication with said at least one independent fluid delivery lumen; and a fluid directing member having a portion located proximately to an intersection of said fluid delivery lumen and said inner lumen, said portion adapted to selectively obstruct flow in either a proximal or a distal direction of said fluid delivery lumen.

2. The intraluminal shunt apparatus of claim 1 wherein said at least one fluid delivery lumen extends between a first discharge port associated with said proximal end and a second discharge port associated with said distal end, said lumen defining a fluid-flow path through said primary tubular member.

3. The intraluminal shunt apparatus of claim 2 wherein said fluid directing member comprises a valve means coupled to said fluid delivery lumen which is adapted to selectively direct said fluid or drug into said fluid delivery lumen and towards either of said first discharge port or said second discharge port.

4. The intraluminal shunt apparatus of claim 3 wherein said valve means comprises a one-way valve.

5. The intraluminal shunt apparatus of claim 1 wherein said primary tubular member is dimensioned and configured to be inserted into a vessel selected from the group consisting of the right or left coronary artery, the posterior descending vein, the atrioventricular nodal branch artery, the left anterior descending artery, the left circumflex, the posterior descending artery, and any marginal branch of the left anterior descending artery.

6. The intraluminal shunt apparatus of claim 5 wherein said primary tubular member is dimensioned and configured to be inserted into the right coronary artery of a heart of a patient.

7. The intraluminal shunt apparatus of claim 1 wherein at least a portion of the outer surface of said primary tubular member is configured to fluidly seal against said vessel.

8. The intraluminal shunt apparatus of claim 1 wherein said primary tubular member includes first and second occlusion members which extend about said primary tubular member, said first and second occlusion members being longitudinally spaced apart to define an occlusion section therebetween which is substantially fluidly sealed from said perfusion path.

9. The intraluminal shunt apparatus of claim 1 wherein each of said proximal and said distal ends of said primary tubular member are beveled.

10. The intraluminal shunt apparatus of claim 1 wherein said primary tubular member is comprised of a silicone material.

11. An intraluminal shunt apparatus for administration of fluid into a vessel while maintaining blood perfusion through the vessel, said apparatus comprising:
    a primary tubular member adapted for insertion into said vessel, said primary tubular member having a proximal end and a distal end;
    at least one blood perfusion lumen defining a perfusion path through the primary tubular member;
    at least one independent fluid delivery lumen extending longitudinally along at least a portion of said primary tubular member; and
    a first and second flange extending from the outer surface of said primary tubular member, said flanges being configured to engage an inner wall of the vessel, said first and second flange extending about said primary tubular member and being longitudinally spaced apart to define an occlusion section therebetween which is substantially fluidly sealed from said perfusion path.

12. An intraluminal shunt apparatus for administration of fluid into a vessel while maintaining blood perfusion through the vessel, said apparatus comprising:
    a primary tubular member adapted for insertion into said vessel, said primary tubular member having a proximal end and a distal end;
    at least one blood perfusion lumen defining a perfusion path through the primary tubular member;
    at least one independent fluid delivery lumen extending between a first discharge port associated with said proximal end and a second discharge port associated with said distal end, said lumen defining a fluid-flow path through said primary tubular member;
    at least one secondary tubular member coupled to said primary tubular member, said secondary tubular member having at least one inner lumen in fluid communication with said at least one independent fluid delivery lumen; and
    a valve means coupled to said secondary tubular member which engages and bifurcates said fluid delivery lumen into a distal delivery lumen and a proximal delivery lumen, said valve means adapted to selectively direct said fluid or drug into either of said distal delivery lumen or said proximal delivery lumen.

13. An intraluminal shunt apparatus for administration of fluid into a vessel while maintaining blood perfusion through the vessel, said apparatus comprising:
    a primary tubular member adapted for insertion into said vessel having a proximal end and a distal end;
    at least one blood perfusion lumen defining a perfusion path through said primary tubular member;
    at least one independent fluid delivery lumen extending between a first discharge port associated with said proximal end and a second discharge port associated with said distal end, said lumen defining a fluid-flow path through said primary tubular member;
    at least one secondary tubular member coupled to said primary tubular member, said secondary tubular member having at least one inner lumen in fluid communication with said at least one independent fluid delivery lumen; and
    a one-way valve comprising a luer connection member which is rotatably coupled to said secondary tubular member; and a tubular rod having a proximal end, a distal end having a discharge opening, and an inside lumen extending from said luer connection to said discharge opening, said discharge opening positioned within said fluid delivery lumen and being rotatable to selectively direct said fluid or drug into said fluid delivery lumen and towards either of said first discharge port or said second discharge port.

14. An intraluminal shunt apparatus for administration of fluid into a vessel while maintaining blood perfusion through the vessel, said apparatus comprising:
    a primary tubular member adapted for insertion into said vessel, said primary tubular member having a beveled proximal end and a beveled distal end wherein at least one of said proximal and distal ends are beveled at an angle from about 30 degrees to about 60 degrees;
    at least one blood perfusion lumen defining a perfusion path through the primary tubular member; and
    at least one independent fluid delivery lumen extending longitudinally along at least a portion of said primary tubular member.

15. A drug delivery apparatus comprising a primary tubular member having a first end and a second end, said primary tubular member sized and dimensioned to be inserted into a vessel of a patient, a secondary tubular member fluidly coupled to said primary tubular member, and said secondary tubular member comprises a fluid delivery means for selectively delivering a pharmaceutical composition from said secondary tubular member through either said first or said second end of said primary tubular member and into the vessel.

16. The drug delivery apparatus of claim 15 wherein said primary tubular member comprises a blood perfusion lumen defining a blood perfusion path through said primary tubular member.

17. The drug delivery apparatus of claim 16 wherein said fluid delivery means comprises an independent inner fluid delivery lumen within said primary tubular member and a valve means coupled to said fluid delivery lumen for selectively permitting the flow of a drug or fluid within said fluid delivery lumen towards either the proximal or distal end of said of said primary tubular member.

18. The drug delivery apparatus of claim 17 wherein said valve means comprises a one-way valve.

19. The drug delivery apparatus of claim 15 wherein said fluid delivery means comprises a drug delivery catheter inserted into said secondary tubular member and extending through the proximal or distal end of the primary tubular member.

20. The drug delivery apparatus of claim 19 wherein said drug delivery catheter has a proximal end, a distal end, at least one inner lumen extending therewithin, and at least one discharge opening at or near the distal end of the catheter which is fluidly coupled to said inner lumen, said catheter having a sufficient length and flexibility to extend transluminally beyond said proximal or distal end of said primary tubular member.

21. The drug delivery apparatus of claim 16 wherein said fluid delivery means comprises a first independent fluid delivery lumen extending generally longitudinally within said primary tubular member towards said distal end and a second independent fluid delivery lumen extending generally longitudinally within said primary tubular member towards said proximal end.

22. A method of inducing reversible ventricular asystole in the heart of a patient while maintaining the ability of the heart to be electrically paced, said method comprising the steps of:
 providing an intraluminal shunt apparatus having a primary tubular member being dimensioned and configured to be inserted into the coronary vessel, said primary tubular member having a proximal end and a distal end, and at least one secondary tubular member coupled to said primary tubular member;
 preparing an opening in the vessel to permit insertion of said proximal end and said distal end of said primary tubular member through said opening;
 inserting the proximal and distal ends of the primary tubular member into the opening in the vessel; and
 delivering a pharmaceutical composition through said secondary tubular member and into said vessel, said pharmaceutical composition capable of inducing reversible ventricular asystole in the heart of a patient while maintaining the ability of the heart to be electrically paced.

23. The method of claim 19 wherein the step of preparing an opening in a coronary vessel comprises making an incision in a coronary vessel selected from the group consisting of the right or left coronary artery, the posterior descending artery, the left anterior descending artery, the posterior descending vein, the atrioventricular nodal branch artery, the left anterior descending artery, the left circumflex, the posterior descending artery, and the first marginal branch of the left anterior descending artery.

24. The method according to claim 20 wherein the step of preparing an opening in a coronary vessel comprises making an incision in the right coronary artery.

25. The method according to claim 21 wherein the step of preparing an opening in a coronary vessel comprises making an incision in the right coronary artery at or near the junction to the atrioventricular nodal branch artery.

26. The method of claim 22 wherein the step of delivering the pharmaceutical composition through said secondary tubular member comprises inserting a drug delivery catheter into said secondary tubular member and delivering the composition through the drug delivery catheter.

27. A method for administering fluid to a desired site within a vessel of a patient while also maintaining blood perfusion through the vessel comprising:
 providing an intraluminal shunt apparatus capable of selectively delivering a pharmaceutical composition through said shunt in either a first direction or a second direction;
 preparing an opening in said vessel;
 inserting at least a portion of said primary tubular member into said opening in the vessel;
 determining a desired direction of delivery for said drug or fluid based upon the position of said shunt relative to said desired site, said delivery direction corresponding to either said first direction or said second direction; and
 selectively delivering a drug or fluid through said shunt in said desired direction.

28. The method according to claim 27 wherein the step of selectively delivering the drug or fluid through said shunt comprises inserting a drug delivery catheter into said shunt, directing said drug delivery catheter in said desired direction, and delivering said drug or fluid through said drug delivery catheter.

* * * * *